United States Patent [19]

Abrahams

[11] Patent Number: 5,305,502
[45] Date of Patent: Apr. 26, 1994

[54] CLAMP

[75] Inventor: Graham N. Abrahams, Lyttleton Manor, South Africa

[73] Assignee: Clampi Corporation CC, Transvaal, South Africa

[21] Appl. No.: 872,009

[22] Filed: Apr. 22, 1992

[30] Foreign Application Priority Data

Apr. 23, 1991 [ZA] South Africa ............. 91/3031

[51] Int. Cl.⁵ ............................................. A44B 21/00
[52] U.S. Cl. .......................................... 24/517; 24/615
[58] Field of Search ............... 24/517, 575, 597, 615, 24/616, 351, 304, 301, 302, 3 J; 63/13

[56] References Cited

U.S. PATENT DOCUMENTS

| 432,177 | 7/1890 | Bernard | 24/517 |
|---|---|---|---|
| 717,367 | 12/1902 | Ellis | 24/517 |
| 1,074,605 | 10/1913 | Carter | 24/517 |
| 1,651,435 | 12/1927 | Bernstein . | |
| 1,738,111 | 12/1929 | Mowry | 24/517 |
| 2,267,331 | 12/1941 | Guyot . | |
| 2,269,662 | 1/1942 | Guyot . | |
| 3,246,376 | 4/1966 | Vazquez . | |
| 3,447,209 | 6/1969 | Sullivan | 24/351 |
| 3,561,077 | 2/1971 | Grant | 24/517 |

FOREIGN PATENT DOCUMENTS

| 668973 | 12/1965 | Belgium . |
|---|---|---|
| 2537410 | 6/1984 | France . |
| 644246 | 8/1964 | South Africa . |
| 2109452 | 6/1983 | United Kingdom . |

Primary Examiner—Victor N. Sakran
Attorney, Agent, or Firm—Burns, Doane, Swecker & Mathis

[57] ABSTRACT

The invention relates to a clamp comprising a first C-shaped jaw having first and second limbs and an interconnecting bight portion. A second jaw is mounted pivotably to the second limb, and a releasable ratchet-and-pawl arrangement is provided for locking the second jaw relative to the first jaw in a number of degrees of closure. A finger-actuable tab is provided on the pawl for releasing the pawl from the ratchet and allowing bidirectional pivoting of the second jaw. The first limb is provided with a circular aperture and the second jaw is arranged to urge material to be clamped between the first and second jaws through the cavity, so as to increase the effectiveness of clamping. The material which has passed through the cavity also serves as a cushion. The clamp is particularly suited for use as a diaper clamp.

11 Claims, 3 Drawing Sheets

CLAMP

BACKGROUND TO THE INVENTION

The invention relates to a clamp, and in particular to a clamp for securing diapers.

Many conventional clamps have opposed jaws which are biased towards one another by a resilient member, such as a spring. Lever arms are usually provided on each jaw to force the jaws apart. The jaws of these clamps are generally biased fairly strongly towards one another, which makes them unsuited to applications such as the fastening of diapers, as they may tend to pinch the baby wearing the diaper if carelessly applied. Furthermore, an outer face of one of the jaws is liable to bear against the infant's skin, which may lead to irritation.

SUMMARY OF THE INVENTION

According to the invention there is provided a clamp comprising a first jaw which includes a first limb, a second opposed limb and an interconnecting bight portion extending between the first and second limbs; a second jaw being mounted pivotably towards the free end of the second limb; locking means for locking the second jaw relative to the first jaw in a plurality of degrees of closure; and release means for releasing the locking means, the first limb terminating in an aperture and the free end of the second jaw being pivotable towards the aperture for urging a portion of material to be clamped between the first and second jaws into the aperture.

Preferably, the locking means comprises a ratchet, a pawl component, and biasing means integral with the pawl component for biasing the pawl component into engagement with the ratchet and allowing unidirectional movement of the second jaw towards the aperture in the first limb.

Conveniently, the ratchet is formed at the pivoted end of the second jaw and the pawl component is carried by the second limb.

In a preferred form of the invention, the release means comprises a finger-engagable tab integral with the pawl component for compressing the biasing means and disengaging the pawl component from the ratchet to allow bidirectional pivotal movement of the second jaw.

Advantageously, the second limb comprises a pair of spaced apart parallel fingers, jaw mounting means being located towards the free ends of the fingers for pivotably mounting the pivoted end of the second jaw between the fingers, and pawl mounting means being located rearwardly of the jaw mounting means for mounting the pawl component pivotably between the fingers.

In a preferred form of the invention the clamp includes a web having a landing surface extending between the pair of fingers, the biasing means on the pawl component being in the form of a rearwardly extending leaf spring which abuts the landing surface, and the release means being arranged above the leaf spring for compressing the leaf spring against the landing surface.

The jaw and pawl mounting means are preferably in the form of respective front and rear pairs of apertures, a pair of front stub axles extend laterally from opposite sides of the pivoted end of the second jaw for pivotal engagement with the front pair of apertures and a pair of rear stub axles extend laterally from opposite sides of the pawl component for pivotal engagement with the rear pair of apertures.

Conveniently, the fingers are elastically deformable, the lower ends of the rear stub axles are chamfered, an axle-receiving channel extends downwardly from an upper edge of each finger along an inner face thereof to each rear aperture, for facilitating the introduction of the stub axles into the rear apertures in a snap fit during assembly of the clamp.

The ratchet and pawl may be recessed or flush relative to a side profile of the second limb.

The free end of the second jaw preferably describes a locus which extends into the aperture, the free end being provided with material-engaging formations for urging a portion of material through the aperture and proud of the outer surface of the first limb for providing a cushioning effect.

In an alternative form of the invention, the pawl component may be formed integrally with the second limb, the pawl component being connected to the second limb by means of a resilient neck which serves as a spring for biasing the pawl component against the ratchet.

The clamp may be formed from three separate unitary components, namely the first jaw, the second jaw and the pawl component.

All the components of the clamp are preferably moulded from a plastics material.

In one common application, the clamp is adapted for use as a diaper clamp for clamping the ends of a diaper together.

DESCRIPTION OF EMBODIMENTS

Figure 1:
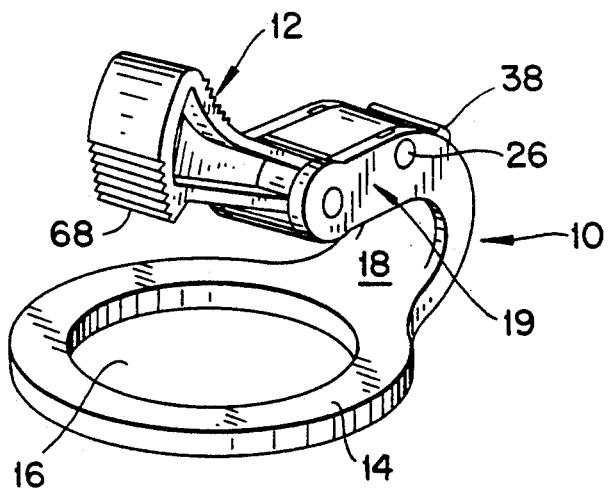
FIG. 1 shows a perspective view of a first embodiment of a clamp of the invention in the open position.

The clamp illustrated in FIGS. 1 to 6 comprises a first C-shaped jaw 10 and a second jaw 12. The first jaw 10 has a first lower ring-shaped limb 14 defining a circular aperture 16. A curved bight portion 18 interconnects the lower ring-shaped limb 14 with a second upper limb 19 comprising a pair of fingers 20 and 22. A sprung pawl component 24 is mounted pivotably between the fingers 20 and 22 on a pair of stub axles 26 and 28 which nest in complemental circular apertures 30 and 32 formed towards the base of the fingers.

The sprung pawl component 24 is provided with an integrally moulded resilient foot which serves as a leaf spring 34. The free end of the leaf spring 34 bears against a web having planar landing surface 36 which extends transversely between the fingers 20 and 22 at the upper end of the bight portion 18. Located just above the leaf spring 34 is a finger-engagable tab 38, the upper surface of which is provided with serrations 40. A tooth 42 projects from the front end of the pawl. The tooth 42 is engagable with an arcuate toothed ratchet arrangement 44 formed at the pivoted end of the second jaw 12. The tooth 42 is biased into engagement with complemental recesses 46 in the toothed ratchet arrangement by virtue of the leaf spring 34 bearing against the landing surface 36. In order to release the tooth 42 from the ratchet arrangement 44, the thumb or finger is pressed downwardly against the serrations 40 on the upper surface of the tab 38, thereby compressing the spring 34 and disengaging the tooth 42 from the recess 46 in the ratchet arrangement 44 so as to allow free bidirectional pivoting of the second jaw 12 relative to the first jaw 14.

Figure 5:
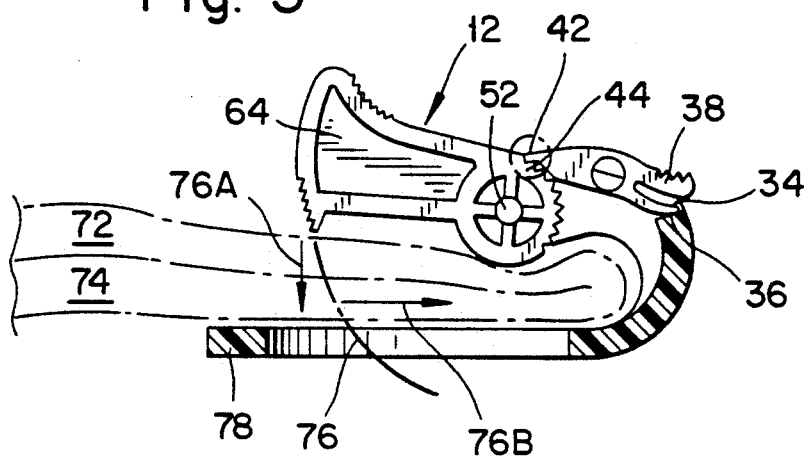
FIG. 5 shows a cross-sectional side view of the clamp in the open position on the line 5—5 of FIG. 4.
Figure 5A:
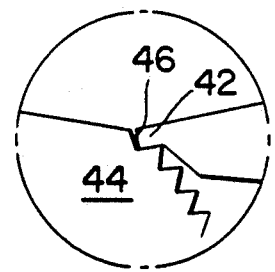
FIG. 5A is a fragmentary enlargement of FIG. 5.

The second jaw 12 is provided with a pair of stub axles 50 and 52 which locate in respective circular apertures 54 and 56 defined in circular formations 58 and 60 at the free end of the fingers 20 and 22. The second jaw 12 pivots on the stub axles 50 and 52 between an open position illustrated in FIGS. 1 and 5 and a closed position indicated in FIGS. 2 and 6. The second jaw 12 is essentially of hollow construction, having recesses 62 and 64 divided by a central web 66. The free end of the second jaw 12 terminates in a claw 68, the front face of which is provided with material-engaging serrations 70. With the second jaw 12 in the open position, as is illustrated in FIGS. 1 and 5, the clamp can be clamped over the ends 72 and 74 of a diaper. The second jaw 12 is then pressed downwards to the closed position illustrated in FIGS. 2 and 6, the claw 68 of the second jaw describing a circular arc or locus 76 which has both downward and inward components as is illustrated by arrows 76A and 76B. The claw 68 and the serrations 70 snag the outer surface of the diaper end 72. The diaper ends 72 and 74 are thus drawn both rearwardly towards the bight portion 18 and downwardly through the circular aperture 16. The diaper ends 72 and 74 tuft through the aperture 16, as is illustrated at 75 in FIG. 6. As a result, the infant's skin is spaced apart and cushioned from the outer surface 78 of the first jaw by means of the tufted portion, which stands proud of the outer surface 78. In the normal closed position, no portion of the clamp is therefore actually in contact with the skin of an infant.

The various components of the clamp illustrated in FIGS. 1 to 6, namely the first jaw 10, the second jaw 12 and the pawl component 24 are specially designed for easy and automated assembly. The fingers 20 and 22 are elastically deformable, and can be biased ontwardly. The stub axles 26 and 28 on the pawl 24 have chamfered lowered ends 80. Channels 82 and 84 lead from the upper edges and along the inner faces of the fingers 20 and 22 to the apertures 30 and 32. In order to locate the stub axles 26 and 28 within the apertures 30 and 32, the fingers 20 and 22 are merely splayed slightly apart and the chamfered lower portions 80 of the stub axles 26 and 28 are guided into the channels 82 and 84. The pawl 24 is then pushed downwards, which causes the stub axles 26 and 28 to engage the apertures 30 and 32 in a snap fit. The second jaw 12 is then fitted by merely splaying the fingers 20 and 22 and inserting the stub axles 50 and 52 into the apertures 54 and 56.

Figure 6:
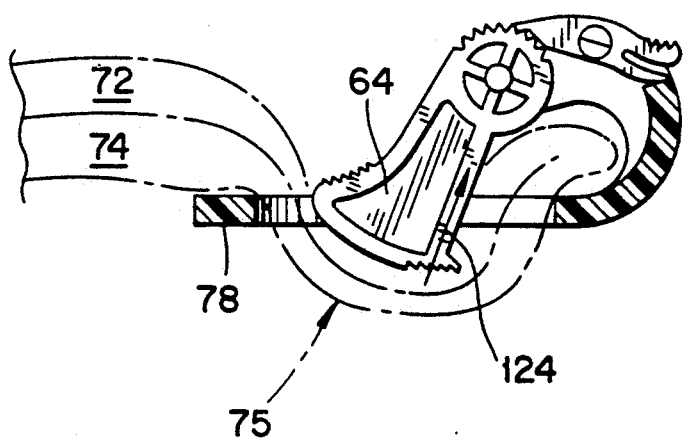
FIG. 6 shows a similar cross-section to that of FIG. 5 with the clamp in the closed position.
Figure 7:
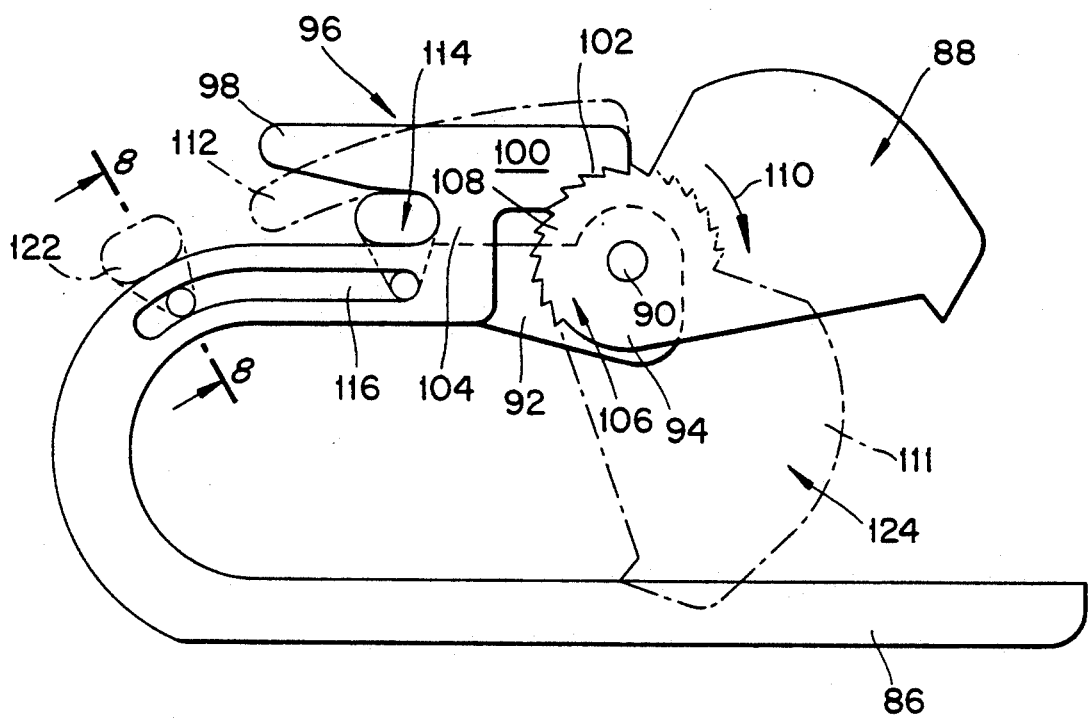
FIG. 7 shows a side view of a second embodiment of a clamp of the invention.
Figure 8:
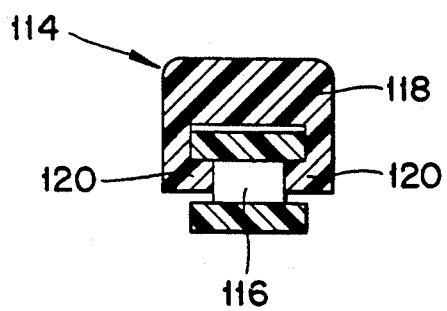
FIG. 8 shows a cross-section on the line 8—8 of FIG. 7.

Referring now to FIGS. 7 and 8, a second embodiment of a clamp of the invention is shown. A first jaw 86 has the same basic C-shaped configuration as the jaw 10 illustrated in FIGS. 1 to 6. A second jaw 88 is hinged pivotably to the first jaw 86 about an imaginary axis 90. A tongue 92 protrudes from the front portion of the upper limb of the first jaw 86, and extends between a clevis, formed at the rear of the second jaw 88, only one &/rk 94 of which can be seen in FIG. 6. A pawl component 96 is moulded integrally with the first jaw 86, the pawl component having a rearwardly extending finger-actuable tab 98 and a forwardly extending pawl portion 100 having a plurality of saw teeth 102 formed therein. The pawl component 96 is joined to the upper limb of the first jaw 86 by means of a resilient neck 104.

The second jaw 88 has a arcuate ratchet arrangement 106 constituted by a plurality of saw teeth 108. As is clear from the drawing, the saw teeth 102 and 108 mesh complementally with one another. The second jaw 88 is able to pivot in the direction of arrow 110, as the shallow inclined surfaces of the respective saw teeth 102 and 108 are able to glide over one another, to a closed position indicated in broken outline at 111. The second jaw 88 is unable to pivot in the opposite direction as the steep faces of the saw teeth 102 and 108 bear against one another and interlock.

In order to disengage the saw teeth from one another, the tab 98 is depressed downwardly to a position indicated in broken outline at 112, which effectively causes the pawl component 96 to pivot about the neck 104, thereby raising and freeing the saw teeth 102 from the saw teeth 108. This allows the second jaw 88 to pivot back to the open position.

A locking formation 114 may optionally be provided for locking the pawl 96 in the engaged position. The locking formation 114 is constituted by a slot 116 which extends through the upper limb of the first jaw. A C-shaped slide 118 has re-entrant portions 120 which hold the slide 118 captive within the slot 116. The slide 118 is moveable from a locked position to a released position, indicated in broken outline at 122, which allows the tab 98 to be depressed so as to release the ratchet arrangement 106.

The clamp illustrated in the first and second embodiments is formed entirely from a plastics material such as acetal, which is non-toxic and which will not react to urine or faeces. The dye which colours the acetal is likewise non-toxic and non-reactive. Furthermore, the plastics material has a smooth finish 7hich allows it to be cleaned easily. The rounded edges and minimal protrusions reduce the possibility of the baby being injured, as the rounded edges are not able to pierce or scratch the skin of the baby. The ratchet arrangement illustrated in both the first and second embodiments is recessed away from the outer surface of the clamp, thereby reducing the possibility of the teeth of the pawl or ratchet coming into direct contact with the skin of the infant. It is only the smooth, rounded outer edges which contact the infant. As was described earlier on in the specification, the circular aperture in the first jaw accommodates a tufted portion of the diaper which extends beyond the lower outer surface of the clamp and cushions the infant's skin against direct contact with the clamp.

Figure 2:
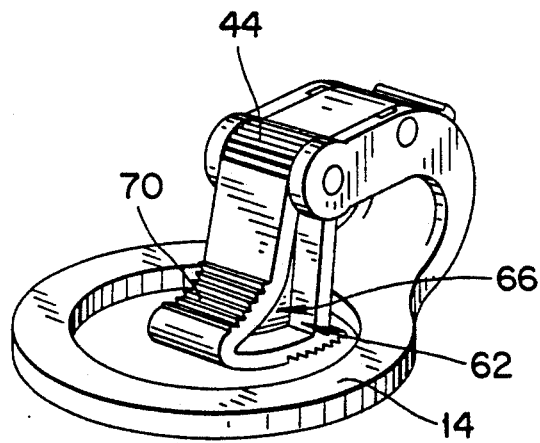
FIG. 2 shows a perspective view of the clamp of FIG. 1 in the closed position.
Figure 3:
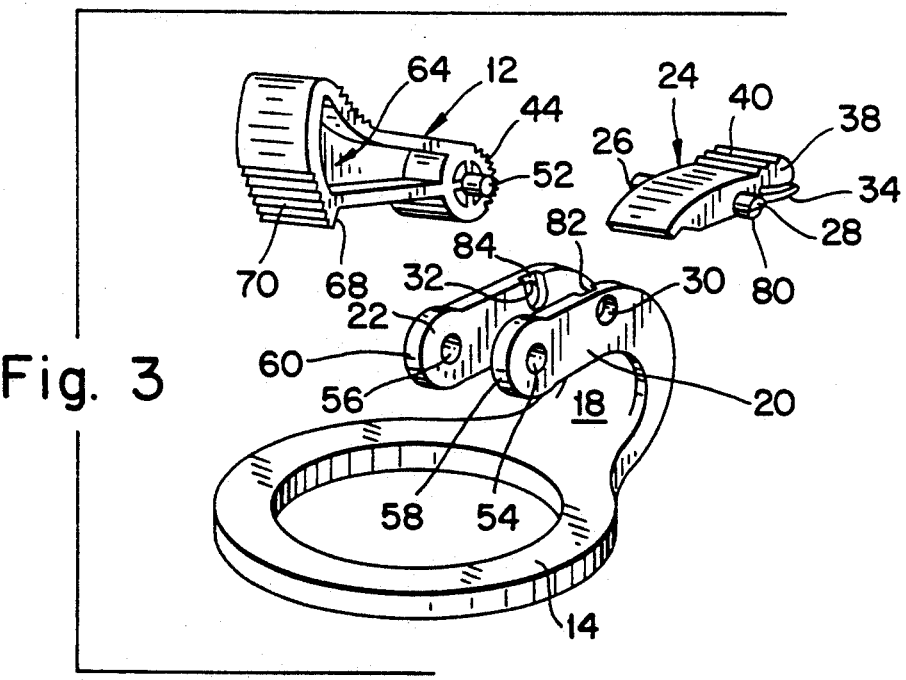
FIG. 3 shows an exploded view of the various components making up the clamp of FIGS. 1 and 2.
Figure 4:
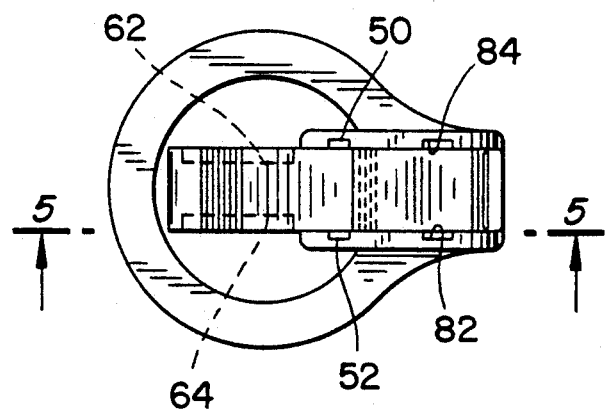
FIG. 4 shows a top plan view of the first embodiment of the clamp in the open position.

In the closed position indicated in FIGS. 2 and 6, and in broken outline in FIG. 7, the first jaw experiences a moment of force in the direction of arrow 124, which is directed substantially towards the axis of rotation of the first jaw. This force, relative to the ratchet teeth, is radial rather that tangential, 7hich serves to place minimal strain on the ratchet teeth, and thereby allows a less robust and a potentially less harmful ratchet-and-pawl arrangement to be used, in which the teeth and serrations are too small to scratch or irritate the skin of the infant.

Owing to the ratchet and pawl, the degree of closure of the second jaw is variable, thereby providing for different thicknesses of material to be clamped.

The clamp of the invention is not confined to a diaper clamp, but may be used in many applications, for instance as a papaer clip or as a heavy duty clamp in industrial applications, in which case it would be fabricated from steel.

I claim:

1. A clamp comprising a first jaw which includes first limb, a second opposed limb and an interconnecting bight portion extending between the first and second limbs; a second jaw being mounted pivotably towards the free end of the second limb; locking means for locking the second jaw relative to the first jaw in a plurality of degrees of closure; and release means for releasing the locking means, the first limb terminating in an aperture, and the free end of the second jaw being pivotable towards the aperture for urging a portion of material to be clamped between the first and second jaws into the aperture, the locking means comprising a ratchet, a pawl component, and biasing means for biasing the pawl component into engagement with the ratchet and allowing unidirectional movement of the second jaw towards the aperture in the first limb.

2. A clamp as claimed in claim 1 in which the ratchet is formed at the pivoted end of the second jaw and the pawl component is carried by the second limb.

3. A clamp as claimed in claim 1 in which the release means comprises a finger-engagable tab integral with the pawl component for compressing the biasing means and disengaging the pawl component from the ratchet to allow bidirectional pivotal movement of the second jaw.

4. A clamp as claimed in claim 1 in which the second limb comprises a pair of spaced apart parallel fingers, jaw mounting means being located towards the free ends of the fingers for pivotably mounting the pivoted end of the second jaw between the fingers, and pawl mounting means being located rearwardly of the jaw mounting means for mounting the pawl component pivotably between the fingers.

5. A clamp as claimed in claim 4 in which a web having a landing surface extends between the pair of fingers, the biasing means component being in the form of a leaf spring which extends rearwardly from the pawl and abuts the landing surface, and the release means is arranged above the leaf spring for compressing the leaf spring against the landing surface.

6. A clamp as claimed in claim 5 in which the jaw and pawl mounting means are in the form of respective front and rear pairs of apertures, a pair of front stub axles extend laterally from opposite sides of the pivoted end of the second jaw for pivotal engagement with the front pair of apertures and a pair of rear stub axles extend laterally from opposite sides of the pawl component for pivotal engagement with the rear pair of apertures.

7. A clamp as claimed in claim 6 in which the fingers are elastically deformable, the lower ends of the rear stub axles are chamfered, and an axle-receiving channel extends downwardly from an upper edge of each finger along an inner face thereof to each rear aperture, for facilitating the introduction of the stub axles into the apertures in a snap fit during assembly of the clamp.

8. A clamp as claimed in claim 1 in which the ratchet and pawl are recessed or flush relative to a side profile of the second limb.

9. A clamp as claimed in claim 1 in which the pawl component is formed integrally with the second limb, the pawl component being connected to the second limb by means of a resilient neck which serves as a spring defining the biasing means for biasing the pawl component against the ratchet.

10. A clamp as claimed in claim 1 in which the free end of the second jaw describes a locus which extends into the aperture, the free end being provided with material-engaging formations for urging a portion of material through the aperture and proud of the outer surface of the first limb for providing a cushioning effect.

11. A clamp as claimed in claim 1, wherein the biasing means is integral with the pawl component.

* * * * *